(12) United States Patent
Lowe

(10) Patent No.: US 9,421,288 B2
(45) Date of Patent: Aug. 23, 2016

(54) CUVETTE APPARATUS

(71) Applicant: Thomas J. Lowe, Eagle, MI (US)

(72) Inventor: Thomas J. Lowe, Eagle, MI (US)

( * ) Notice: Subject to any disclaimer, the term of this patent is extended or adjusted under 35 U.S.C. 154(b) by 553 days.

(21) Appl. No.: 13/789,848

(22) Filed: Mar. 8, 2013

(65) Prior Publication Data
US 2013/0248459 A1 Sep. 26, 2013

Related U.S. Application Data

(60) Provisional application No. 61/613,835, filed on Mar. 21, 2012.

(51) Int. Cl.
| | | |
|---|---|---|
| *A61L 2/10* | (2006.01) | |
| *A61L 2/08* | (2006.01) | |
| *C02F 1/32* | (2006.01) | |
| *F15D 1/00* | (2006.01) | |
| *F15D 1/02* | (2006.01) | |
| *B01F 5/00* | (2006.01) | |

(52) U.S. Cl.
CPC . *A61L 2/10* (2013.01); *A61L 2/084* (2013.01); *C02F 1/325* (2013.01); *F15D 1/0005* (2013.01); *A61L 2202/22* (2013.01); *C02F 2201/328* (2013.01); *C02F 2201/3222* (2013.01); *C02F 2201/3227* (2013.01); *C02F 2301/024* (2013.01); *C02F 2301/026* (2013.01); *Y10T 137/0318* (2015.04)

(58) Field of Classification Search
CPC .. A61M 39/00; A61M 1/3681; A61L 2/0047; A61L 2/10; A61L 2/084; A61L 2/0052; C02F 1/325; C02F 1/32; C02F 2201/32; C02F 2201/3222; C02F 2201/328; C02F 2303/04; F15D 1/0005; B01F 5/0612; B01F 5/0618; B01F 2005/0625; B01F 2005/0627; B01F 2005/0637
USPC .................................................. 366/336, 340
See application file for complete search history.

(56) References Cited

U.S. PATENT DOCUMENTS

| | | | |
|---|---|---|---|
| 4,068,830 A * | 1/1978 | Gray | B01F 5/0451 366/175.2 |
| 4,428,744 A | 1/1984 | Edelson | |
| 4,866,282 A | 9/1989 | Miripol et al. | |
| 5,429,594 A | 7/1995 | Castle | |

(Continued)

FOREIGN PATENT DOCUMENTS

| | | | |
|---|---|---|---|
| DE | 19531751 | * 11/1996 | ............... A61M 1/36 |
| DE | 10 2013 204297 A1 | 9/2013 | |
| WO | WO-2004/016152 A2 | 2/2004 | |

*Primary Examiner* — Krishnan S Menon
*Assistant Examiner* — Bradley R Spies
(74) *Attorney, Agent, or Firm* — Schwegman Lundberg & Woessner, P.A.

(57) ABSTRACT

Blood or other fluid can be treated with UV or other light, such as using an apparatus that can include a cuvette. The cuvette can include an elongated tube configured to permit passage of light of a desired wavelength into the tube, which can include a fluid inlet at a first end and a fluid outlet at a longitudinally opposing second end. A turbulator within the tube can include a helical baffle segment configured to induce mixing and rotation of fluid flow about a longitudinal axis of the tube. The method can include passing a fluid, from a fluid inlet at a first end of an elongated tube to a fluid outlet at a longitudinally opposing second end of the elongated tube. Mixing and rotational flow of the fluid can be induced within the tube about a longitudinal axis of the tube and light of a desired wavelength can be permitted into the tube.

12 Claims, 5 Drawing Sheets

(56) References Cited

U.S. PATENT DOCUMENTS

| | | |
|---|---|---|
| 5,770,147 A | 6/1998 | Muller |
| 5,868,695 A | 2/1999 | Wolf, Jr. et al. |
| 5,951,509 A | 9/1999 | Morris |
| 6,113,566 A | 9/2000 | Schleicher |
| 6,193,681 B1 | 2/2001 | Davidner et al. |
| 6,245,570 B1 | 6/2001 | Grimm et al. |
| 6,951,548 B1 | 10/2005 | Einstein |
| 2003/0179648 A1* | 9/2003 | Heusser ............... B01F 5/0617 366/336 |
| 2003/0205454 A1* | 11/2003 | Hlavinka ........... A61K 41/0019 204/157.15 |
| 2004/0186412 A1 | 9/2004 | Mallett et al. |
| 2006/0270960 A1 | 11/2006 | Karp |
| 2006/0283786 A1* | 12/2006 | Harbers .................... A61L 9/20 210/85 |
| 2007/0083144 A1 | 4/2007 | Petrie |
| 2007/0181823 A1 | 8/2007 | Baumeister |
| 2008/0056065 A1* | 3/2008 | Keller .................. B01F 5/0612 366/339 |
| 2011/0240266 A1 | 10/2011 | Holland |

\* cited by examiner

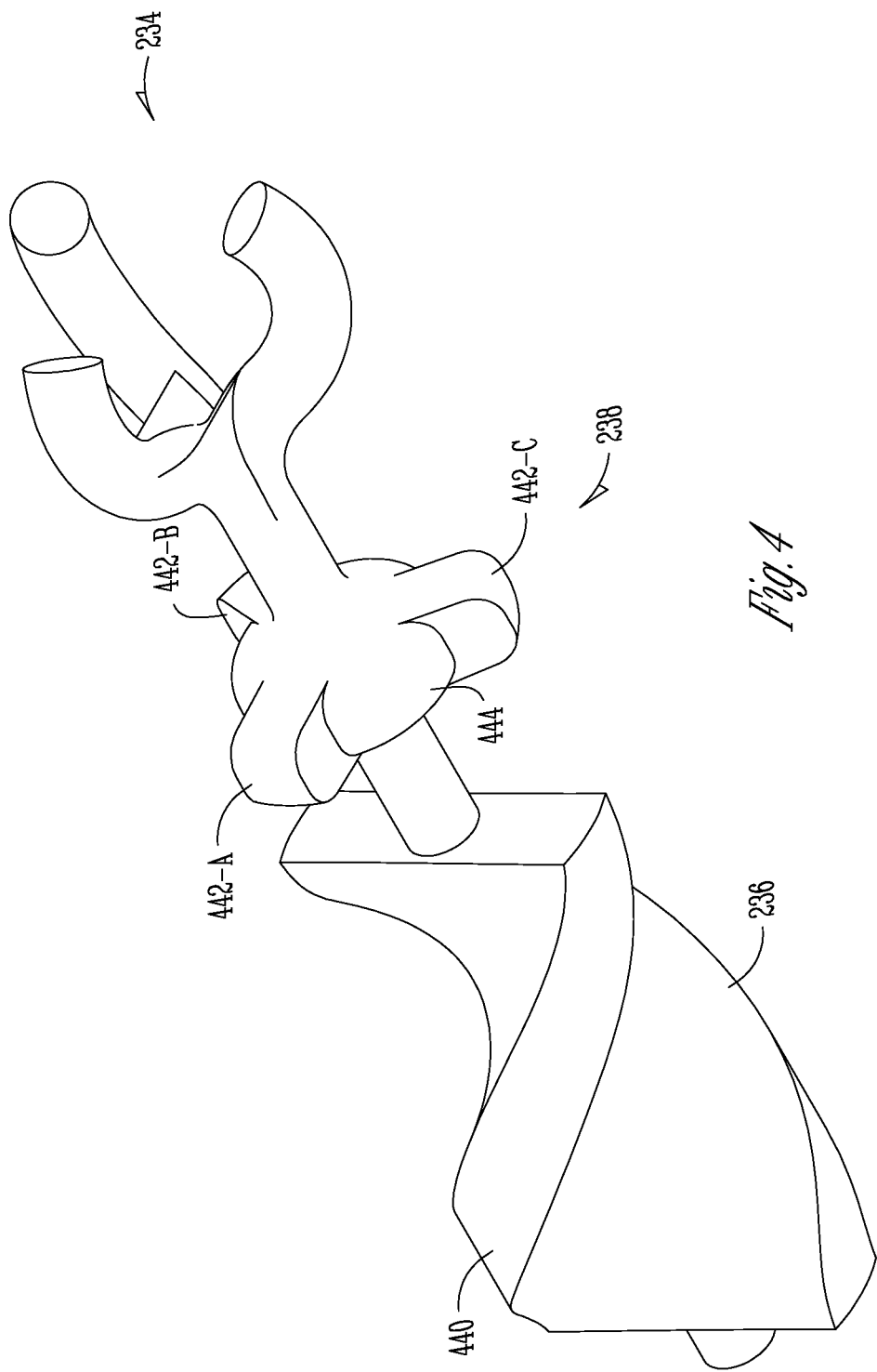

550 ─╮

552
PASSING A FLUID, FROM A FLUID INLET AT A FIRST END OF AN ELONGATED TUBE TO A FLUID OUTLET AT A LONGITUDINALLY OPPOSING SECOND END OF THE ELONGATED TUBE

554
INDUCING MIXTION OF FLOW OF THE FLUID WITHIN THE TUBE

556
SERIALLY ROTATING FLUID FLOW ABOUT A LONGITUDINAL AXIS OF THE TUBE BY MULTIPLE INSTANCES OF AN AT LEAST 45 DEGREE ROTATION

558
INDUCING THE FLUID FLOW OUTWARDLY FROM THE LONGITUDINAL AXIS TOWARD THE INNER SURFACE OF THE ELONGATED TUBE

560
SERIALLY NON-HELICALLY DEFLECTING THE FLUID FLOW BETWEEN ADJACENT INSTANCES OF THE AT LEAST 45 DEGREE ROTATION

562
PERMITTING PASSAGE OF LIGHT OF A DESIRED WAVELENGTH INTO THE TUBE

564
EXPOSING THE FLUID WITHIN THE TUBE TO ULTRAVIOLET (UV) LIGHT

*Fig. 5*

CUVETTE APPARATUS

CLAIM OF PRIORITY

This application claims the benefit of priority of Lowe, U.S. Provisional Patent Application Ser. No. 61/613,835, entitled "CUVETTE APPARATUS AND METHOD," filed on Mar. 21, 2012, which is herein incorporated by reference in its entirety.

BACKGROUND

Fluid treatment devices can take a number of approaches depending on an intended end-use of the fluid or an intended end-composition of the fluid. For example, carbon filtering can be used to remove a number of contaminants from water so that the water is fit for human consumption. Irradiation devices can involve exposing a fluid to ultraviolet (UV) light. Irradiation can disassociate biological or chemical structures within the fluid. For example, a blood transfusion procedure can involve adding riboflavin to donor blood and exposing the riboflavin-donor blood mixture to UV light for five to ten minutes. This can cause an irreversible inactivation of infectious pathogens.

U.S. Pat. No. 6,113,566 is directed toward an ultraviolet blood irradiation method and apparatus.

U.S. Patent Pub. No. 20070083144A1 is directed toward a blood irradiation system device.

SUMMARY

The present inventor has recognized, among other things, that fluid irradiation can be used in a number of industries including, but not limited to, the water purification industry or the health care industry. For example, a cuvette designed to impart turbulence on a fluid passing through the cuvette and configured to permit passage of an ultraviolet wavelength light through a wall of the cuvette can be used to irradiate blood during a blood transfusion procedure. To better illustrate the cuvette apparatus and related method disclosed herein, a non-limiting list of examples is provided here:

Example 1 can include or use subject matter (e.g., an apparatus or method) such as an apparatus that can comprise a cuvette. The cuvette can include an elongated tube, that can be configured to permit passage of light of a desired wavelength into the tube. The tube can include a fluid inlet at a first end and a fluid outlet at a longitudinally opposing second end. The cuvette can further include a turbulator, which can be located within the tube. The turbulator can include a helical baffle segment that can be configured to induce mixing and rotation of fluid flow, between the fluid inlet and the fluid outlet, about a longitudinal axis of the tube.

Example 2 can optionally include or use, or can optionally be combined with the subject matter of Example 1 to include or use, the turbulator including a series of helical baffle segments, individually including an edge of at least 45 degree rotation about the longitudinal axis of the tube, and a series of non-helical baffle segments, individually interspersed between adjacent helical baffle segments in the series of helical baffle segments.

Example 3 can optionally include or use, or can optionally be combined with the subject matter of any one or any combination of Examples 1 or 2 to include or use, the helical baffle segment being optionally sized, shaped, or otherwise configured to increase a fluid flow rate at or around the helical baffle segment and to slow the flow rate at or around (e.g., prior to) the non-helical baffle segment.

Example 4 can include or use, or can optionally be combined with the subject matter of any one or any combination of Examples 1-3 to include or use, the non-helical baffle segments individually including a blade extending perpendicularly from the longitudinal axis.

Example 5 can include or use, or can optionally be combined with the subject matter of any one or any combination of Examples 1-4 to include or use, the helical baffle segment being sized, shaped, or otherwise configured to provide an angular displacement of the fluid flow of at least 45 degrees about the longitudinal axis of the tube.

Example 6 can include or use, or can optionally be combined with the subject matter of any one or any combination of Examples 1-5 to include or use, the helical baffle segment being sized, shaped, or otherwise configured to induce the fluid flow outwardly from the longitudinal axis toward an inner surface of the elongated tube.

Example 7 can include or use, or can optionally be combined with the subject matter of any one or any combination of Examples 1-6 to include or use, an ultraviolet (UV) light source.

Example 8 can include or use, or can optionally be combined with the subject matter of any one or any combination of Examples 1-7 to include or use a reflector that can be sized, shaped, or otherwise configured to expose at least a portion of a length of the cuvette to reflected UV light.

Example 9 can include or use, or can optionally be combined with the subject matter of any one or any combination of Examples 1-8 to include or use, the helical baffle segment including an edge that can be sized, shaped, or otherwise configured to interrupt the fluid flow and induce mixing of the fluid.

Example 10 can include or use, or can optionally be combined with the subject matter of any one or any combination of Examples 1-9 to include or use, a diode light source.

Example 11 can include or use, or can optionally be combined with the subject matter of any one or any combination of Examples 1-10 to include or use, the turbulator including a prong at an end of the turbulator. The prong can be sized, shaped, or otherwise configured to secure the turbulator to the tube.

Example 12 can include or use subject matter (e.g., a method or an apparatus), or can optionally be combined with the subject matter of one or any combination of Examples 1-11 to include or use, passing a fluid, from a fluid inlet at a first end of an elongated tube to a fluid outlet at a longitudinally opposing second end of the elongated tube. The subject matter can further comprise inducing mixing and rotational flow of the fluid within the tube about a longitudinal axis of the tube and permitting passage of light of a desired wavelength into the tube.

Example 13 can include or use, or can optionally be combined with the subject matter of any one or any combination of Examples 1-12 to optionally include serially rotating fluid flow about the longitudinal axis of the tube by multiple instances of an at least 45 degree rotation, and serially non-helically deflecting the fluid flow between adjacent instances of the at least 45 degree rotation.

Example 14 can include or use, or can optionally be combined with the subject matter of any one or any combination of Examples 1-13, to optionally include or use inducing the fluid flow outwardly from the longitudinal axis toward an inner surface of the elongated tube.

Example 15 can include or use, or can optionally be combined with the subject matter of any one or any combination of Examples 1-14 to optionally include or use, exposing the fluid within the tube to visible light.

Example 16 can include or use, or can optionally be combined with the subject matter of any one or any combination of Examples 1-15 to include or use, exposing the fluid within the tube to ultraviolet (UV) light.

Example 17 can include or use, or can optionally be combined with the subject matter of any one or any combination of Examples 1-16 to include or use, controlling exposure of the fluid to a light emitting diode source by limiting a current.

Example 18 can include or use, or can optionally be combined with the subject matter of any one or any combination of Examples 1-17 to include or use, controlling an ambient temperature in or about the tube.

Example 19 can include or use, or can optionally be combined with the subject matter of any one or any combination of Examples 1-18 to include or use, diluting the fluid with a saline solution, before supplying the fluid to the turbulator.

Example 20 can include or use subject matter (e.g., an apparatus or a method), or can optionally be combined with the subject matter of one or any combination of Examples 1-19 to include or use a cuvette, including an elongated tube. The elongated tube can be configured to permit passage of light of a desired wavelength into the tube. The tube can include a fluid inlet at a first end and a fluid outlet at a longitudinally opposing second end. The subject matter can further include or use a turbulator, such as within the tube. The turbulator can include or use a series of helical baffle segments, which can individually include an edge of an at least 45 degree rotation about the longitudinal axis of the tube, and which can be individually sized, shaped, or otherwise configured to induce mixing of the fluid and to induce fluid flow outwardly from the longitudinal axis toward an inner surface of the elongated tube. The subject matter can include or use a series of non-helical baffle segments, which can be individually interspersed between adjacent helical baffle segments in the series of helical baffle segments.

In Example 21, the apparatus or method of any one or any combination of Examples 1-20 can be optionally configured such that all elements or options recited are available to use or select from.

These and other examples and features of the present cuvette apparatus and methods will be set forth in part in the following Detailed Description. This Summary is intended to provide non-limiting examples of the present subject matter—it is not intended to provide an exclusive or exhaustive explanation. The Detailed Description below is included to provide further information about the present cuvette apparatus and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4 shows an example of a detailed view of a subsection of the turbulator of FIG. 3, in accordance with at least one example.

FIG. 5 is a flow chart of an example of a fluid treatment method, such as can use a cuvette and turbulator, in accordance with at least one example.

DETAILED DESCRIPTION

The present disclosure relates generally to a fluid treatment apparatus and method, such as can include or use a cuvette for containing (e.g., holding or carrying) fluid. The cuvette can include an elongated tube, with a fluid inlet and a fluid outlet, and a turbulator. The turbulator can include a helical baffle segment. The helical baffle segment can be configured to induce mixing and rotational fluid flow, such as about a longitudinal axis of the elongated tube. The cuvette can be configured to permit passage of light into the tube. This can permit exposure of a fluid in the tube to the light.

Figure 1:
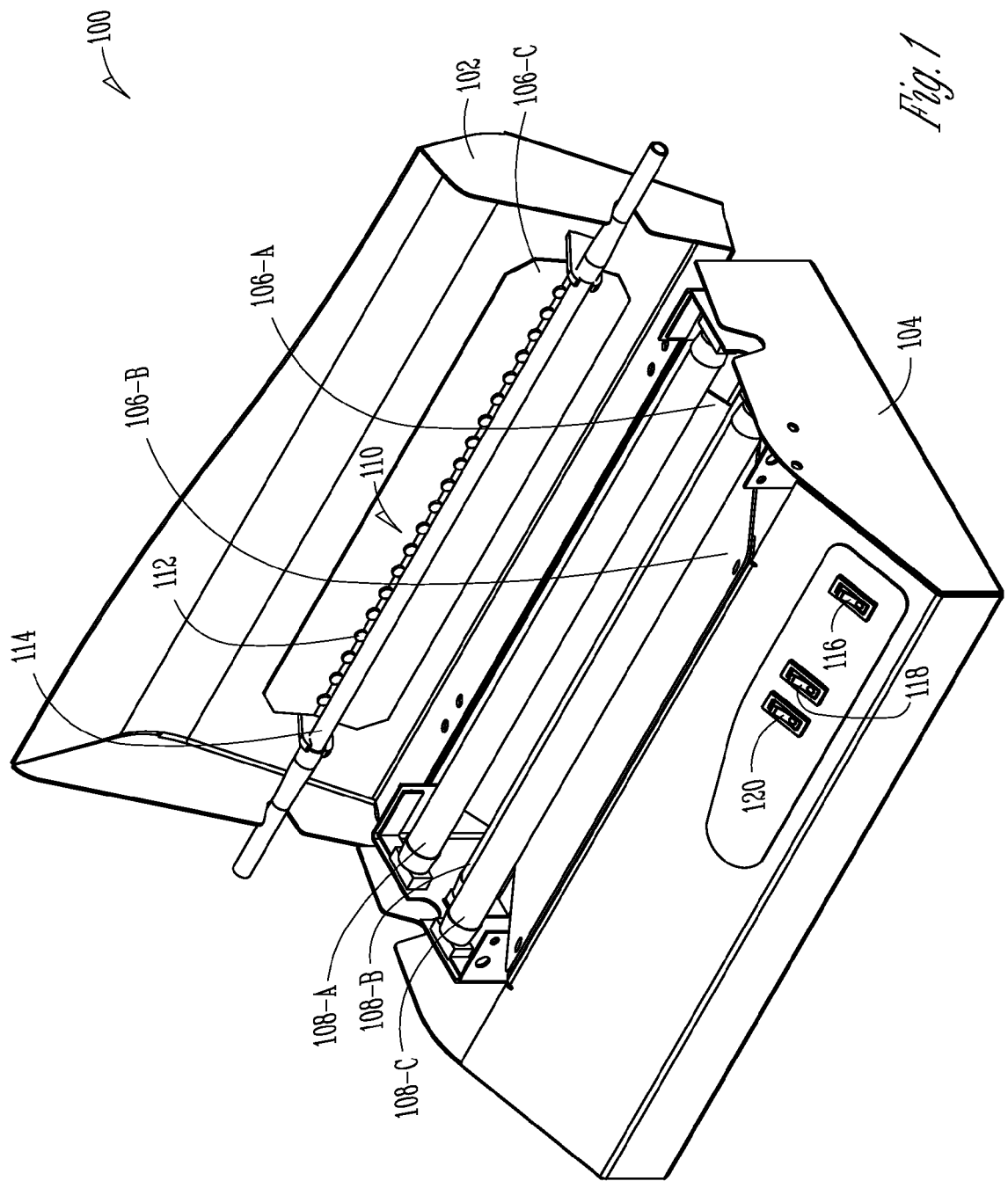
FIG. 1 shows an example of a fluid irradiation apparatus, in accordance with at least one example.

FIG. 1 shows an example of a fluid treatment apparatus 100. The apparatus 100 can include a cuvette 114. The apparatus 100 can be configured to irradiate a fluid, passing through the cuvette 114, such as water, or a bodily fluid such as blood or spinal fluid. The apparatus 100 can include a lid portion 102 and a base portion 104, either or both of which can include one or more reflectors, such as 106-A, 106-B, and 106-C, such as a mirrored surface that can be configured to reflect all or a substantial portion of incident light. Reflectors 106-A and 106-B can be configured to expose at least a portion of a length of the cuvette 114 to reflected ultraviolet light. In an example, the reflectors 106-A, 106-B, and 106-C individually, collectively, or both, can be configured to provide 360 degree light exposure to the cuvette, e.g., reflected light, direct light, or both.

The apparatus 100 can include one or more ultraviolet (UV) light sources 108-A, 108-B, and 108-C, such as can include one or more of a fluorescent light, an incandescent light, a mercury vapor light, or a light emitting diode (LED). One or more of the UV light sources 108-A, 108-B, and 108-C can include one or more of a UVA, UVB, or UVC light source. UVA can include wavelengths in a range of from about 315 nanometers (nm) to about 400 nm. UVB can include wavelengths in a range of from about 280 nm to about 315 nm. UVC can include wavelengths in a range of from about 200 nm to about 280 nm. In an example, the one or more UV light sources 108-A, 108-B, and 108-C can extend along substantially an entire length of the lid 102 or the base 104. In an example, UV light sources 108-A, 108-B, and 108-C can include one or more visual light source.

The apparatus 100 can include a light bar 110, which can include one or more light emitting diode (LED) or other light sources 112. The light bar 110 can extend along all or at least a portion of the length of the cuvette 114. The one or more diode light sources 112 can include a semiconductor light source such as a LED that can be configured to be capable of emitting light at a wavelength that is visible to a human eye, such as at a wavelength in a range of from about 400 nm to about 475 nm.

The apparatus 100 can include one or more switches 116, 118, and 120, which can be configured to: turn on or off one or more of the light sources 108-A, 108-B, and 108-C; turn on or off one or more of the diode light sources 112; turn on or off a fan that can be included in the apparatus 100; regulate a current such as to the one or more of the light sources 108-A, 108-B, and 108-C; or control a temperature sensor that can be included in the apparatus 100. The apparatus 100 can include an automatic shutoff circuit, such as can be configured to turn off the one or more light sources 108-A, 108-B, and 108-C, such as when the lid 102 is open or is separated from the base 104.

Figure 2:
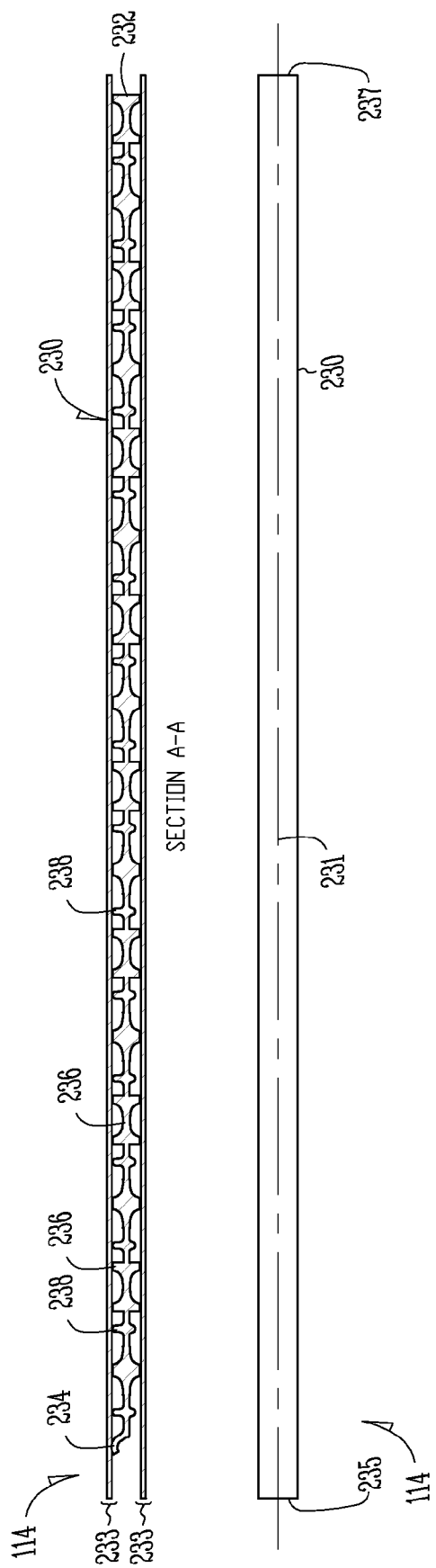
FIG. 2 shows an example of a cuvette, such as can be used in the fluid irradiation apparatus, in accordance with at least one example.

FIG. 2 shows an example of a cuvette 114, such as can be included in or used with the apparatus 100. The cuvette 114 can include an elongated tube 230 defining a longitudinal axis 231 extending lengthwise along the center of the elongated tube 230. The elongated tube 230 can be configured to provide a transparent or translucent tube wall 233 or to otherwise permit passage of light of one or more desired wavelengths into the elongated tube 230. For example, the elongated tube 230 can be configured to permit passage of UV light through a tube wall 233 of the elongated tube 230. The elongated tube 230 can include one or more of UV light penetrable glass, UV light penetrable quartz, UV light penetrable quartz glass, or UV light penetrable plastic, among others. The elongated tube 230 can include a fluid inlet 235 at a first end and a fluid outlet 237 at a longitudinally opposing second end, and can be otherwise sealed to retain or carry fluid within the elongated tube 130. The elongated tube 230 can advantageously permit 360 degree light exposure of a fluid inside the elongated tube 230.

The cuvette 114 can include a turbulator 232 that can be located within the tube 230. The turbulator 232 can include a helical baffle segment 236. The helical baffle segment 236 can be configured to be stationary, but to induce mixing and rotation of passing fluid flow, such as between the fluid inlet 235 and the fluid outlet 237, about the longitudinal axis 231 of the tube 237. For example, the helical baffle segment 236 can be configured to induce turbulent fluid flow. The cuvette 114 can be used in the fluid treatment apparatus 100 such as to provide one or more benefits. Examples of such benefits can include providing a relatively cost-effective cuvette, allowing for varying UV light wavelengths or intensity, increased energy absorbed by the fluid without overheating the fluid or apparatus, as described herein, or a disposable cuvette that can decrease the chance of cross contamination.

Figure 3:
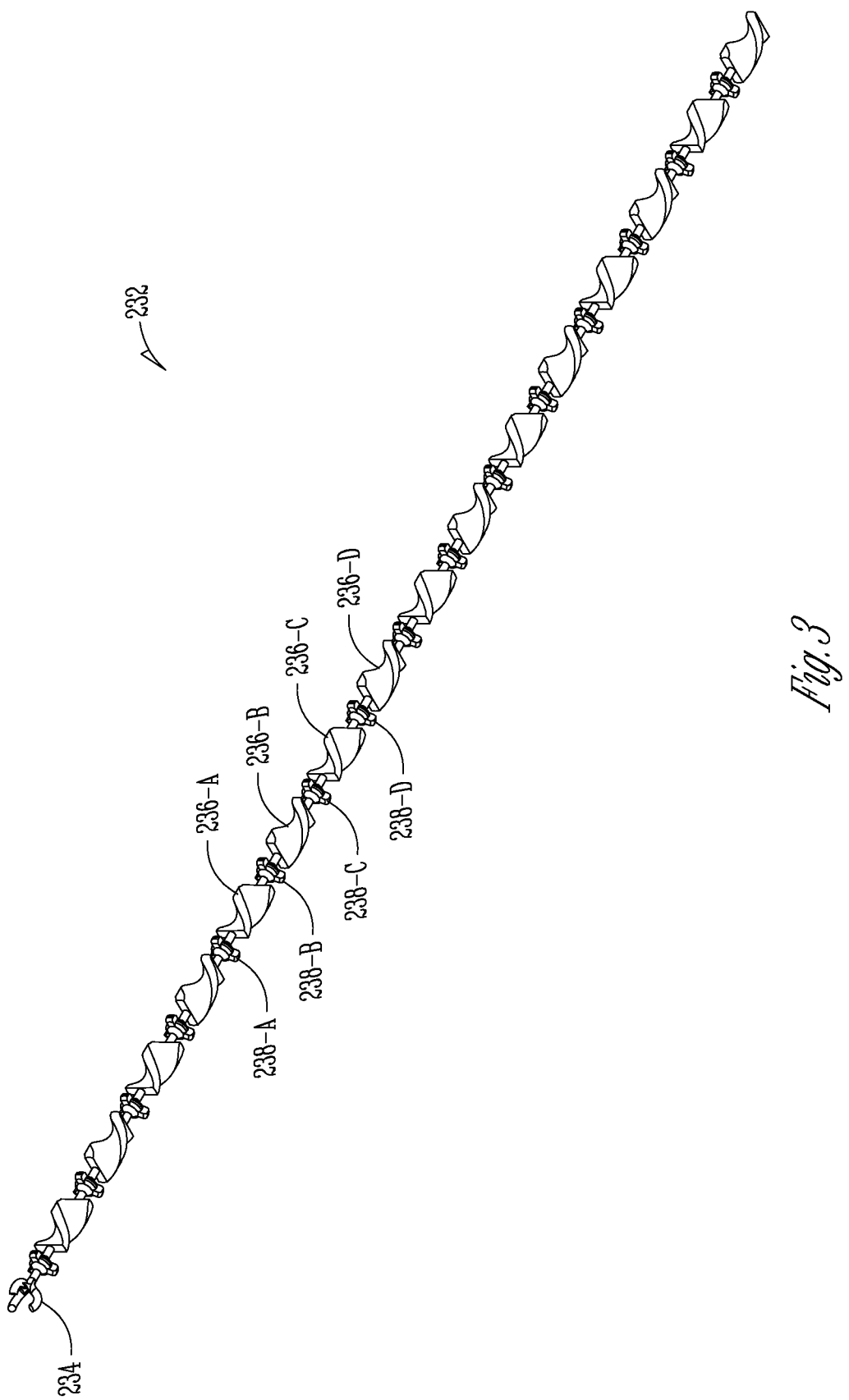
FIG. 3 shows an example of a turbulator, such as can be used in the cuvette, in accordance with at least one example.

FIG. 3 shows an example of a turbulator 232, such as can be inserted coaxially into an elongated tubular cuvette such as described herein. The turbulator 232 can include a series of helical baffle segments 236-A, 236-B, 236-C, and 236-D. An individual helical baffle segment 236-A, 236-B, 236-C, and 236-D can include an edge, which can spiral about a longitudinal axis (FIG. 2, 231) of the turbulator 232 such as to provide an at least a 45 degree rotation (inducing a like rotation in fluid flow) about the longitudinal axis (FIG. 2, 231) for that particular helical baffle segment. For example, FIG. 4 shows an example of a helical baffle segment that can have an edge 440 that can spiral such as to provide about a 180 degree rotation for that particular helical baffle segment. A turbulator 232 can include a single helical baffle segment (e.g., of at least a 45 degree rotation) or, as shown in the example of FIG. 3, can include a series of such helical baffle segments, such as to serially induce like rotations in fluid flow by the same or different amounts.

The turbulator 232 can include a series of non-helical baffle segments 238-A, 238-B, 238-C, and 238-D, which can respectively be interspersed between adjacent helical baffle segments 236-A, 236-B, 236-C, and 236-D in the series of helical baffle segments. An individual helical baffle segment 236-A, 236-B, 236-C, and 236-D can be configured to permit an increased rate of fluid flow at or around the helical baffle segments 236-A, 236-B, 236-C, and 236-D, e.g., relative to the fluid flow rate between such helical baffle segments. Interspersed therebetween can be non-helical baffle segments 238-A, 238-B, 238-C, and 238-D, which can be configured to decrease the rate of fluid flow around the non-helical baffle segments, e.g., relative to the fluid flow rate at the helical baffle segments. Flow around the helical baffle segments 236-A, 236-B, 236-C, and 236-D or non-helical baffle segments 238-A, 238-B, 238-C, and 238-D can include fluid flowing on a portion or all sides of the non-helical baffle segment. Serially increasing and decreasing the fluid flow rate can help induce turbulence or mixing of the fluid, such as via one or more of eddies, recirculation, or induced apparent randomness of the fluid. This can increase fluid exposure to light (e.g., UV light or visible light), such as by bringing fluid from the center of the cuvette to its interior periphery, where it can receive incident light that passes through the cuvette wall. The helical baffle segments 236-A, 236-B, 236-C, and 236-D can be sized or shaped or otherwise configured to induce the fluid to flow outwardly from the longitudinal axis (FIG. 2, 231) toward an inner surface of the elongated tube. Such outward fluid flow can move the fluid toward or into an enhanced light penetration zone, such as described herein. Turbulent flow can optionally additionally be enhanced by adjusting a pressure of the fluid within the cuvette (e.g., using a valve or nozzle) and additionally or alternatively including or using an acoustic transducer in contact with or in acoustic communication with the cuvette to insonify the fluid, such as to cause cavitation of the fluid, such as described in United States Patent Application 20040016699.

The turbulator 232 can include a prong 234 at one or both ends of the turbulator 232. The prong 234 can be configured to secure the turbulator 232 such as to the tube (FIG. 2, 230). The turbulator 232 can provide or enhance turbulent fluid flow between the fluid inlet (FIG. 2, 235) and the fluid outlet (FIG. 2, 237) of the cuvette. Turbulent fluid flow can help inhibit or prevent overheating of the fluid on the inner surface of the elongated tube. Overheating can occur if the temperature of the fluid or of the inner surface of the elongated tube reaches a temperature capable of causing an undesirable reaction because of excessive heat. Turbulent fluid flow can help control temperature, such as by reducing or eliminating the occurrence of hot-spots within the cuvette that could otherwise result from exposure of laminar fluid flow within the elongated tube to light. A fan within the apparatus can also help control the temperature surrounding the cuvette, such as to help inhibit or eliminate overheating. The turbulent fluid flow can also help to mix fluid and to direct well-mixed fluid toward an inner surface of the cuvette, where it is more easily treated by UV light passing through the cuvette wall. The turbulator 232 can include a UV light penetrable material, which can help further expose regions of the fluid to UV light, which can enhance the effectiveness of the UV light treatment of the fluid.

FIG. 4 shows an example of a detailed view of a subsection of the turbulator 232 of FIG. 3. FIG. 4 shows an example of a prong 234, a helical baffle segment 236, and a non-helical baffle segment 238. The helical baffle segment 236 can include an edge 440, which can provide at least a 45 degree spiral rotation about the longitudinal axis of the tube. The example of the edge 440 as shown in FIG. 4 can include a spiral rotation of about 180 degrees about the longitudinal axis of the tube. The edge 440 can be configured to do one or more of interrupting the fluid flow, guiding the fluid, and inducing mixing of the fluid. For example, the helical baffle segment 236 can be configured to provide an angular displacement of the fluid flow of at least 45 degrees about the longitudinal axis of the tube. Interruption of fluid flow, mixing, or angular displacement of fluid flow can help increase exposure of the fluid to light, which can enhance the light treatment of the fluid.

The non-helical baffle segment 238 can include a blade 442-A, 442-B, and 442-C, such as can extend perpendicularly from the longitudinal axis of the turbulator or its coaxially concentrically aligned tube. The blade 442-A, 442-B, and 442-C of FIG. 4 can extend perpendicularly from a hub 444. The blade 442-A, 442-B, and 442-C can be configured to slow or to interrupt flow of the fluid between adjacent helical baffle segments 236-A, 236-B, 236-C, and 236-D.

An example of a method of use can include passing a fluid, from a fluid inlet (FIG. 2, 235) at a first end of an elongated tube to a fluid outlet (FIG. 2, 237) at a longitudinally opposing second end of the elongated tube (FIG. 2, 230), inducing mixing and rotational flow of the fluid within the tube about a longitudinal axis (FIG. 2, 231) of the tube, and permitting passage of light of a desired wavelength into the tube.

FIG. 5 illustrates an example that can include a method 550 of using a cuvette. At 552, a fluid can be passed from a fluid inlet at a first end of an elongated tube to a fluid outlet at a longitudinally opposing second end of the elongated tube. The fluid can be pumped or can pass under the force of gravity (e.g., gravity fed). The fluid flow rate can be controlled, such as by a pump or flow regulator, such as in the path of fluid flow, for example, outside of the cuvette. The fluid flow rate can effect a residency time of the fluid within the cuvette, so as to help control an amount of time the fluid is potentially exposed to light. For example, the fluid flow rate can be increased, so as to decrease the amount of time the fluid is potentially exposed to light.

At 554, mixing of the fluid within the tube can be induced. Mixing can include eddies, rotation, or apparent induced randomness of the fluid flow. Mixing can be observed or determined, by, for example, a Reynolds number (Re) within a turbulent zone. A turbulent zone Re can include a value of about 5000 or greater, which can indicate the presence of mixing.

At 556, fluid flow can be serially rotated about a longitudinal axis of the tube such as by multiple instances of an at least 45 degree rotation. The 45 degree rotation can include using a helical baffle segment with such an edge spiral rotation, such as described herein.

At 558, fluid flow can be induced outwardly from the longitudinal axis toward an inner surface of the elongated tube. This can help increase the exposure of the fluid to light or can help control temperature such as to avoid overheating.

At 560, fluid flow can be non-helically deflected, such as serially between adjacent instances of the at least 45 degree rotation.

At 562, light of a desired wavelength can be permitted to pass into the tube, such as to treat the fluid. The desired wavelength light can include UV light or visible light, or both. The light can be produced by the apparatus, such as from a light source or a diode light source, such as described herein.

At 564, the fluid within the tube can be exposed to UV light, visible light, or both, such as described herein. The exposure of the fluid to UV light can be controlled, such as by limiting a current delivered to a light source, such as by amplitude control, duty-cycling, pulse width modulation (PWM), or other technique. In an example, the current can be controlled via a switch included by the apparatus (FIG. 1, 116, 118, and 120).

In an example, the light (e.g., UV light or visible light) can partially penetrate the fluid within the cuvette. For example, the fluid can be such that light can penetrate to about 3 to 4% of the depth of the fluid. In such an example, an elongated tube with an inner diameter of 6 millimeters (mm) can, with steady state laminar fluid flow, have a light penetration zone from about 0.18 mm to about 0.24 mm of fluid. However, the present techniques can use the turbulator for one or more of inducing mixing, serially rotating the fluid about the longitudinal axis, inducing fluid flow outwardly from the longitudinal axis, or serially non-helically deflecting the fluid, such as can cause turbulent flow and can increase the amount of fluid exposed to the light. For example, the fluid can circulate such as to be within the light penetration zone (e.g., from about 0.18 mm to about 0.24 mm) at one or more locations between the fluid inlet (FIG. 2, 235) and the fluid outlet (FIG. 2, 237). Optically dense fluids can be passed from the fluid inlet to the fluid outlet of the cuvette, as described herein, so as to increase exposure of the optically dense fluid to light, such as increasing an amount of time the optically dense fluid resides in the optically dense fluid specific light penetration zone.

In an example, the fluid exposed to UV light includes blood, such as animal blood or human blood. In such an example, the blood can be drawn from an animal or human and passed (e.g., circulated) through the apparatus, such as to expose the blood to light, and reintroduced back into the animal or human, such as by a closed-looped system. Exposure of the circulated blood to light, such as UV light, can help promote an immune response by inactivating pathogens within the circulated blood. In an example, a portion of the pathogens within the circulated blood are inactivated. The amount of blood drawn can be about 20 milliliters (mL) per 100 pounds of the animal or human. Exposing the blood to light can help to provide energy, such as photonic energy, of around about 500 joules per square meter to about 1000 joules per square meter, to hemoglobin of the blood.

In an example, the fluid exposed to UV light includes water. The water can pass through the apparatus from a fluid inlet to a fluid outlet. The fluid inlet can be connected to a container of water or a continuous supply. In such an example, exposing the water to UV light can help to kill or destroy microorganisms within the water, such as by destroying nucleic acids in the microorganisms. The water can pass through a number of apparatuses in series, each configured to kill or destroy a designated microorganism, such that the end product can be suitable for human consumption or human use.

The method can include controlling an ambient temperature within the apparatus, such as using a fan. The fan can be user-controlled, such as by user-actuating a switch (FIG. 1, 116, 118, and 120), or can be automatically controlled without requiring user intervention, such as via a control loop. The control loop can include a temperature sensor within the apparatus or at the fluid outlet. When a specified threshold temperature value is reached or exceeded, the fan can be activated, such as to circulate air within the apparatus to reduce the ambient temperature within the apparatus.

The method can include, before supplying the fluid to the turbulator, diluting the fluid, such as with a compatible dilution fluid (e.g., wherein the fluid is blood being subjected to UV light treatment). This can lower a viscosity of the fluid or lower optical density of the fluid, so as to increase exposure of the fluid to light or increase energy absorbed by the fluid. The dilution can include, for example, 1 part saline to four parts fluid.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A blood treatment apparatus, comprising:
a cuvette, including:
an elongated tube, having a transparency or translucency permitting passage of light of a desired wavelength for treating blood into the tube, the tube including a fluid inlet at a first end and a fluid outlet at a longitudinally opposing second end; and
a turbulator, within the tube and fixed with respect to the tube, the turbulator including:
a series of helical baffle segments, extending from a longitudinal shaft extending along a longitudinal axis, configured to induce mixing and rotation of fluid flow, between the fluid inlet and the fluid outlet, about the longitudinal axis of the tube, the helical baffle segments individually including an edge of at least 45 degree rotation about the longitudinal axis of the tube; and
a series of blood flow accelerating non-helical baffle segments, individually interspersed between adjacent helical baffle segments in the series of helical baffle segments, the non-helical baffle segments individually presenting a larger edge cross-sectional area than the helical baffle segments to blood flowing in a direction generally parallel to the longitudinal axis of the tube, wherein the blood flow accelerating non-helical baffle segments individually include:
a central disk-shaped hub portion extending radially outward from the longitudinal shaft; and
at least three blades extending further radially outward from the central disk-shaped hub portion to reach an inner surface of the tube, thereby defining bloodflow regions between adjacent blades and the tube, through which accelerating blood is directed to flow toward an inner surface of the tube to allow light of a desired wavelength into the tube and to penetrate the blood.

2. The apparatus of claim 1, wherein
the non-helical baffle segments individually including the at least three blades being substantially equally spaced from each other.

3. The apparatus of claim 2, wherein the non-helical baffle segment includes a constriction that is configured to increase a fluid flow rate and is separated from the helical baffle segment by a reduced cross-section shaft region defining an enlarged fluid flow region that is configured to slow the fluid flow rate prior to the helical baffle segment.

4. The apparatus claim 2, wherein the non-helical baffle segments and their corresponding hubs define a reduced cross-sectional area of faster fluid flow relative to the helical baffle segments.

5. The apparatus of claim 1, wherein the helical baffle segment is configured to provide an angular displacement of the fluid flow of at least 45 degrees about the longitudinal axis of the tube.

6. The apparatus of claim 1, wherein the helical baffle segment is configured to induce the fluid flow outwardly from the longitudinal axis toward an inner surface of the elongated tube.

7. The apparatus of claim 1, including an ultraviolet (UV) light source.

8. The apparatus of claim 1, including a reflector configured to expose at least a portion of a length of the cuvette to reflected UV light.

9. The apparatus of claim 1, wherein the non-helical baffle segment includes an edge that is configured to interrupt the fluid flow and the helical baffle segment includes a blade that is configured to induce mixing of the fluid.

10. The apparatus of claim 1, including a diode light source.

11. The apparatus of claim 1, wherein the turbulator includes a prong at an end of the turbulator, the prong configured to secure the turbulator to the tube.

12. A blood treatment apparatus, comprising:
a cuvette, including:
an elongated tube, having a transparency or translucency permitting passage of light of a desired wavelength into the tube, the tube including a fluid inlet at a first end and a fluid outlet at a longitudinally opposing second end; and
a turbulator, within the tube and fixed with respect to the tube, the turbulator including:
a series of helical baffle segments, individually including an edge of an at least 45 degree rotation about the longitudinal axis of the tube and individually configured to induce mixing of the fluid and induce fluid flow outwardly from the longitudinal axis toward an inner surface of the elongated tube; and
a series of blood flow accelerating non-helical baffle segments, individually interspersed between adjacent helical baffle segments in the series of helical baffle segments wherein the non-helical baffle segments and their corresponding hubs define a reduced cross-sectional area of fluid flow relative to the helical baffle segments wherein the blood flow accelerating non-helical baffle segments individually include:
a central disk-shaped hub portion extending radially outward from the longitudinal shaft; and
at least three blades extending further radially outward from the central disk-shaped hub portion to reach an inner surface of the tube, thereby defining bloodflow regions between adjacent blades and the tube, through which accelerating blood is directed to flow toward an inner surface of the tube to allow light of a desired wavelength into the tube and to penetrate the blood.

* * * * *